(12) United States Patent
Hirasada et al.

(10) Patent No.: US 10,005,742 B2
(45) Date of Patent: *Jun. 26, 2018

(54) METHOD FOR PRODUCING EPOXY COMPOUND CONTAINING HYDROGEN PEROXIDE STABILIZER

(71) Applicant: NISSAN CHEMICAL INDUSTRIES, LTD., Tokyo (JP)

(72) Inventors: Kazuki Hirasada, Funabashi (JP); Yutaro Tsuda, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/504,054

(22) PCT Filed: Aug. 11, 2015

(86) PCT No.: PCT/JP2015/072765
§ 371 (c)(1),
(2) Date: Feb. 15, 2017

(87) PCT Pub. No.: WO2016/027735
PCT Pub. Date: Feb. 25, 2016

(65) Prior Publication Data
US 2017/0275258 A1    Sep. 28, 2017

(30) Foreign Application Priority Data
Aug. 20, 2014 (JP) ................................ 2014-167244

(51) Int. Cl.
| | | |
|---|---|---|
| C07D 251/34 | (2006.01) |
| C07D 301/12 | (2006.01) |
| C07D 251/04 | (2006.01) |
| C07D 201/16 | (2006.01) |

(52) U.S. Cl.
CPC ......... *C07D 251/34* (2013.01); *C07D 201/16* (2013.01); *C07D 251/04* (2013.01); *C07D 301/12* (2013.01)

(58) Field of Classification Search
CPC ... C07D 301/12; C07D 405/14; C07D 251/34
USPC ....................................................... 544/221
See application file for complete search history.

(56) References Cited

U.S. PATENT DOCUMENTS

| | | | | |
|---|---|---|---|---|
| 4,476,314 A * | 10/1984 | Kuriyama | ............ | C07D 303/04 |
| | | | | 549/526 |
| 7,528,269 B2 * | 5/2009 | Le-Khac | .............. | C07D 301/12 |
| | | | | 549/531 |
| 7,528,314 B2 * | 5/2009 | Puryear | ................ | G10H 1/0066 |
| | | | | 84/600 |
| 8,021,609 B2 * | 9/2011 | Doetsch | .................. | A61L 2/186 |
| | | | | 134/15 |
| 9,464,074 B2 * | 10/2016 | Kakiuchi | ............. | C07D 405/14 |
| 2002/0127231 A1 * | 9/2002 | Schneck | ............ | C07K 14/7051 |
| | | | | 424/178.1 |
| 2002/0127281 A1 * | 9/2002 | Tsao | ..................... | A61K 9/0048 |
| | | | | 424/616 |

FOREIGN PATENT DOCUMENTS

| | | |
|---|---|---|
| JP | S58-39676 A | 3/1983 |
| JP | S60-136577 A | 7/1985 |
| JP | 2009-523126 A | 6/2009 |
| JP | 2009-256217 A | 11/2009 |
| JP | 2012-025688 A | 2/2012 |
| JP | WO2014/065239 A1 | 5/2014 |

OTHER PUBLICATIONS

Oct. 27, 2015 Written Opinion issued in International Patent Application No. PCT/JP2015/072765.
Oct. 27, 2015 International Search Report issued in International Patent Application No. PCT/JP2015/072765.

\* cited by examiner

*Primary Examiner* — Venkataraman Balasubramanian
(74) *Attorney, Agent, or Firm* — Oliff PLC

(57) ABSTRACT

The present invention provides a method for producing an epoxy compound by a reaction of an olefin compound with hydrogen peroxide, wherein the epoxy compound is stably and safely produced using a hydrogen peroxide stabilizer for reducing an oxygen gas generated from hydrogen peroxide. A method for producing an epoxy compound by a reaction of an olefin compound with hydrogen peroxide, wherein the reaction is carried out in the presence of an organophosphorus compound in such a reaction medium that the pH is maintained within a range of more than 7.5 and less than 12.0. The olefin compound may be 1,3,5-tris-(alkenyl)-isocyanurate. The alkenyl group in the olefin compound may be 3-butenyl group, 4-pentenyl group, 5-hexenyl group, 6-heptenyl group, or 7-octenyl group. The epoxy compound may be 1,3,5-tris-(epoxyalkyl)-isocyanurate. The reaction medium may be such a reaction medium that the pH is maintained within a range of 8.0 to 10.5.

9 Claims, No Drawings

METHOD FOR PRODUCING EPOXY COMPOUND CONTAINING HYDROGEN PEROXIDE STABILIZER

TECHNICAL FIELD

The present invention relates to a method for producing an epoxy compound from an olefin compound. In addition, the present invention relates to a method for efficiently producing an epoxy compound by a reaction of hydrogen peroxide, a nitrile compound, and an alkaline substance with an olefin compound having a specific structure in a solvent.

BACKGROUND ART

In general, since a crystalline epoxy resin has a rigid main chain skeleton and is multifunctional, the epoxy resin has high heat resistance. Therefore, such a resin is used in a field requiring heat-resistant reliability, for example, in an electrical and electronic field.

However, in some fields, molding such as casting molding is impossible for some applications unless a liquid composition is used. Therefore, use of the crystalline epoxy resin is restricted to an application using a solid material such as transfer molding, and the range of use of the crystalline epoxy resin is limited.

Conventionally, an epoxy resin used in liquid molding such as casting molding is a liquid epoxy resin, and cannot sufficiently meet a demand for improvement in physical properties of a cured product, such as heat resistance, that is strongly demanded in fields of adhesion, casting, sealing, molding, laminating, and the like in recent years. Therefore, liquefaction of a crystalline multifunctional epoxy resin that imparts physical properties of a cured product having high heat resistance is increasingly demanded.

As a method for producing such an epoxy compound, proposed is a method of epoxidizing an olefin in an acidic medium by a reaction of olefin-substituted isocyanurate using hydrogen peroxide as an oxidizer and a mixed catalyst containing tungstate or molybdate, a surfactant (using a quaternary ammonium salt as a phase-transfer catalyst), and phosphates or phosphonates as a catalyst (see Patent Document 1).

A method for producing an epoxy compound by a reaction of aqueous hydrogen peroxide solution with an olefin compound using a tungsten compound having an epoxidation performance as a catalyst in an acidic medium is disclosed, and aminomethylphosphonic acid is used as a promoter (see Patent Document 2).

Further, a method for producing an epoxy compound by a reaction of an olefin compound, hydrogen peroxide, a nitrile compound, and an alkaline substance in a solvent is disclosed (see Patent Document 3).

PRIOR ART DOCUMENTS

Patent Documents

Patent Document 1: Japanese Patent Application Publication No. 2012-025688 (JP 2012-025688 A)

Patent Document 2: Japanese Patent Application Publication No. 2009-256217 (JP 2009-256217 A)

Patent Document 3: International Publication WO 2014/065239

SUMMARY OF THE INVENTION

Problem to be Solved by the Invention

When an epoxy compound is produced by a reaction of an olefin compound with hydrogen peroxide, hydrogen peroxide is added in an excess amount relative to the olefin compound. At this time, an oxygen gas is generated from hydrogen peroxide. Therefore, it is necessary that the oxygen gas concentration in a reactor be decreased to a concentration of lower explosion limit in terms of safety of a process.

As a method of decreasing the concentration of oxygen gas generated from hydrogen peroxide in the reactor to a safe concentration, exhausting the gas out of the reactor using a flow of nitrogen gas is considered.

In the case of a small-scale reaction, a decrease in oxygen gas in the reactor by a flow of nitrogen gas is a useful means. However, in the case of a large-scale reaction, the flow of nitrogen gas has its limit, and some measures are required.

An object of the present invention is to provide a method for producing an epoxy compound by a reaction of an olefin compound with hydrogen peroxide, wherein the epoxy compound is stably and safely produced using a hydrogen peroxide stabilizer for decreasing an oxygen gas generated from hydrogen peroxide.

Means for Solving the Problems

A first aspect of the present invention is a method for producing an epoxy compound by a reaction of an olefin compound with hydrogen peroxide, wherein the reaction is carried out in the presence of an organophosphorus compound in such a reaction medium that the pH is maintained within a range of more than 7.5 and less than 12.0.

A second aspect is the method according to the first aspect, wherein the olefin compound is 1,3,5-tris-(alkenyl)-isocyanurate.

A third aspect is the method according to the second aspect, wherein the alkenyl group in the olefin compound is 3-butenyl group, 4-pentenyl group, 5-hexenyl group, 6-heptenyl group, or 7-octenyl group.

A fourth aspect is the method according to the first aspect, wherein the epoxy compound is 1,3,5-tris-(epoxyalkyl)-isocyanurate.

A fifth aspect is the method according to the fourth aspect, wherein the epoxyalkyl group in the epoxy compound is 3,4-epoxybutyl group, 4,5-epoxypentyl group, 5,6-epoxyhexyl group, 6,7-epoxyheptyl group, or 7,8-epoxyoctyl group.

A sixth aspect is the method according to any one of the first to fifth aspects, wherein the reaction medium is such a reaction medium that the pH is maintained within a range of 8.0 to 10.5.

A seventh aspect is the method according to any one of the first to sixth aspects, wherein the organophosphorus compound is alkylphosphonic acid or a salt thereof.

An eighth aspect is the method according to any one of the first to seventh aspects, wherein the reaction medium contains a nitrile compound.

A ninth aspect is the method according to the eighth aspect, wherein the nitrile compound is acetonitrile.

A tenth aspect is the method according to any one of the first to ninth aspects, wherein the pH is maintained by addition of an aqueous alkaline solution containing the organophosphorus compound.

An eleventh aspect is the method according to any one of the first to tenth aspects, wherein an amount of the organophosphorus compound added is 0.0001 to 1.0% by mass relative to 1,3,5-tris-(alkenyl)-isocyanurate.

Effects of the Invention

According to the present invention, the generation of an oxygen gas by decomposition of hydrogen peroxide can be decreased. Therefore, an epoxy compound can be stably and safety produced. Accordingly, large-scale production of an epoxy compound is made possible.

MODES FOR CARRYING OUT THE INVENTION

In a method for producing an epoxy compound by a reaction of an olefin compound with hydrogen peroxide, a nitrile compound (e.g., acetonitrile) may be present under an alkaline condition (e.g., sodium hydroxide). In this case, an oxidation active species is produced from hydrogen peroxide, the alkaline substance, and the nitrile compound, and the epoxy compound is produced from the olefin compound.

In general, when a trace amount (e.g., some tens ppb) of heavy metal is present under an alkaline condition, self decomposition of hydrogen peroxide occurs to generate an oxygen gas.

Since this self decomposition does not occur under an acidic condition, a reaction under the acidic condition is out of a problem.

It is considered that a trace amount of the heavy metal is contained in an aqueous alkaline solution (e.g., NaOH aqueous solution). As the reaction proceeds, the heavy metal is accumulated in the reaction system. At the latter half of the whole reaction time, decomposition of hydrogen peroxide is promoted to increase the generation of an oxygen gas. This is a problem in terms of process.

In order to decrease the generation of an oxygen gas by decomposition of hydrogen peroxide due to such a heavy metal, the inventors of the present invention have considered that by an additive of chelating the heavy metal that is considered to cause self decomposition, the decomposition of hydrogen peroxide is suppressed to decrease the generation of an oxygen gas. The inventors have found that the addition of an organophosphorus compound is effective. Thus, the present invention has been completed.

The present invention is a method for producing an epoxy compound by a reaction of an olefin compound with hydrogen peroxide, wherein the reaction is carried out in the presence of an organophosphorus compound in such a reaction medium that the pH is maintained within a range of more than 7.5 and less than 12.0.

The olefin compound as a raw material is, for example, 1,3,5-tris-(alkenyl)-isocyanurate. As the alkenyl group in 1,3,5-tris-(alkenyl)-isocyanurate, for example, 3-butenyl group, 4-pentenyl group, 5-hexenyl group, 6-heptenyl group, or 7-octenyl group may be used, and 3-butenyl group, 4-pentenyl group, or 5-hexenyl group may be preferably used.

The epoxy compound as a product is, for example, 1,3,5-tris-(epoxyalkyl)-isocyanurate. As the epoxyalkyl group in 1,3,5-tris-(epoxyalkyl)-isocyanurate, for example, 3,4-epoxybutyl group, 4,5-epoxypentyl group, 5,6-epoxyhexyl group, 6,7-epoxyheptyl group, or 7,8-epoxyoctyl group may be used, and 3,4-epoxybutyl group, 4,5-epoxypentyl group, or 5,6-epoxyhexyl group may be preferably used.

For example, the olefin compound is represented by Formula (1).

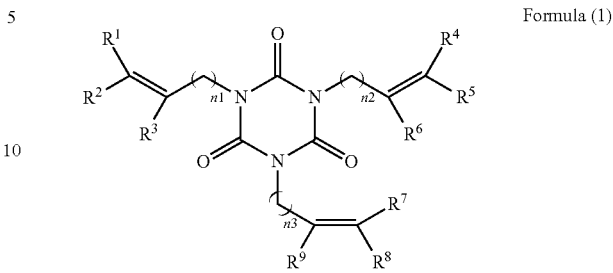

Formula (1)

In Formula (1), $R^1$ to $R^9$ are each independently a hydrogen atom or a methyl group, and n1 to n3 are each independently an integer of 1 to 6. It is preferable that $R^1$ to $R^9$ be each independently a hydrogen atom, and n1 to n3 be each independently an integer of 2 to 6, or 2 to 4.

For example, the epoxy compound is represented by Formula (2).

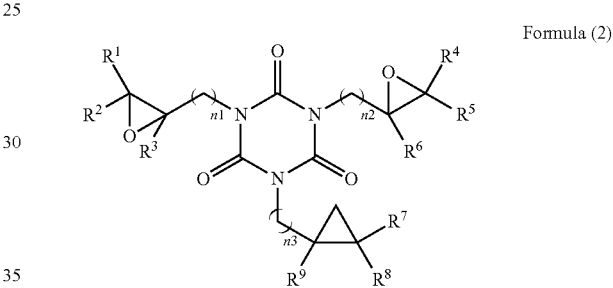

Formula (2)

In Formula (2), $R^1$ to $R^9$ are each independently a hydrogen atom or a methyl group, and n1 to n3 are each independently an integer of 1 to 6. It is preferable that $R^1$ to $R^9$ be each independently a hydrogen atom, and n1 to n3 be each independently an integer of 2 to 6, or 2 to 4.

The amount of hydrogen peroxide used during production of the epoxy compound from the olefin compound is 0.5 to 50 equivalents, 0.5 to 30 equivalents, or 1 to 10 equivalents, relative to 1 equivalent of double bond in the olefin compound. Hydrogen peroxide is added to a reaction system, for example, in a form of 35% by mass aqueous hydrogen peroxide.

Hydrogen peroxide may be all added once, or the predetermined amount of hydrogen peroxide may be sequentially added by a small amount. In the addition of aqueous hydrogen peroxide, a dropping method is applied. Aqueous hydrogen peroxide can be sequentially added by a small amount over the whole reaction time.

Examples of the nitrile compound used during production of the epoxy compound from the olefin compound include an aliphatic nitrile compound and aromatic nitrile. Examples of aromatic nitrile include benzonitrile, and examples of aliphatic nitrile include acetonitrile and propionitrile. In particular, aliphatic nitrile is preferably used, and acetonitrile is more preferably used. The amount of nitrile compound used is 0.5 to 50 equivalents, 1 to 30 equivalents, or 3 to 10 equivalents, relative to 1 equivalent of double bond in the olefin compound.

In the present invention, examples of the alkaline substance used during production of the epoxy compound from the olefin compound include sodium hydroxide, potassium hydroxide, and carbonate-based compounds such as sodium carbonate, potassium carbonate, ammonium carbonate, sodium bicarbonate, potassium bicarbonate, and ammonium bicarbonate. The amount of alkaline substance added is 0.01 to 10 equivalents, or 0.01 to 2 equivalents, relative to 1 equivalent of double bond in the olefin compound.

The organophosphorus compound used in the present invention functions as a hydrogen peroxide stabilizer. Examples thereof include alkylphosphonic acid or a salt thereof.

The alkyl group of alkylphosphonic acid may have a structure in which the group is substituted by a hydroxyl group or an amino group. Further, dimerized di(alkylphosphonic acid) or a salt thereof, or trimerized tri(alkylphosphonic acid) or a salt thereof may be used. Examples of the salts include a sodium salt, a potassium salt, and an ammonium salt.

Examples of the alkylphosphonic acid include 1-hydroxyethane-1,1-diphosphonic acid, nitrilotris(methylenephosphonic acid), N,N,N',N'-ethylenediamine tetrakis(methylenephosphonic acid), methylenediphosphonic acid, aminomethylphosphonic acid, and salts thereof.

In the present invention, the pH of the reaction medium is maintained within a range of more than 7.5 and less than 12.0, and preferably within a range of 8.0 to 10.5.

In order to maintain the pH within such a range, a method of sequentially adding a predetermined amount of an aqueous alkaline solution containing the organophosphorus compound over the whole reaction time may be utilized. The aqueous alkaline solution is an aqueous solution of the alkaline substance. It is preferable that the aqueous alkaline solution containing the organophosphorus compound be added with addition of hydrogen peroxide. For example, the aqueous alkaline solution may be added over the whole reaction time, or according to the time of adding hydrogen peroxide.

A mixed solution in which the organophosphorus compound is contained at a concentration of about 1 to 10,000 ppm, 10 to 1,000 ppm, or 50 to 600 ppm in the aqueous alkaline solution (e.g., NaOH aqueous solution) having a concentration of 0.1 to 60% by mass, 0.1 to 30% by mass, or 1 to 10% by mass, may be added to the reaction system.

In the addition of the organophosphorus compound and the aqueous alkaline solution, the aqueous alkaline solution containing the organophosphorus compound may be added, or the organophosphorus compound and the aqueous alkaline solution may be separately added at the above-described concentrations.

For example, the amount of the organophosphorus compound added is 0.0001 to 10% by mass or 0.0001 to 1.0% by mass relative to 1,3,5-tris-(alkenyl)-isocyanurate.

As a solvent used in the reaction to obtain the epoxy compound from the olefin compound, an alcoholic solvent is used. As the alcoholic solvent, for example, linear, branched, or cyclic alcohol such as methanol, ethanol, ispropanol, n-butanol, tert-amylalcohol, and cyclohexanol may be used. In particular, methanol is preferably used. A non-alcoholic solvent such as toluene may be mixed in the alcoholic solvent.

The reaction to obtain the epoxy compound from the olefin compound can be carried out at a reaction temperature of 5 to 60° C. (typically room temperature of 20° C.) for a reaction time of 5 to 50 hours.

If necessary, a solution after the reaction is filtered to remove an inorganic salt, water is added, and the solvent and the nitrile compound are removed by distillation under reduced pressure to obtain an aqueous phase. The aqueous phase is extracted with chloroform or the like, to obtain an organic phase. The organic phase can be washed by adding an aqueous 1 to 5% by mass sodium thiosulfate solution, an aqueous acid solution (e.g., aqueous 0.1 to 2 N phosphoric acid solution), and pure water by turns. By drying, a product can then be obtained.

A conversion ratio of a double bond in the olefin compound into an epoxy group is 60% or more, for example, 75% or more, or 90% or more.

Examples of the epoxy compound obtained from the olefin compound include as follows.

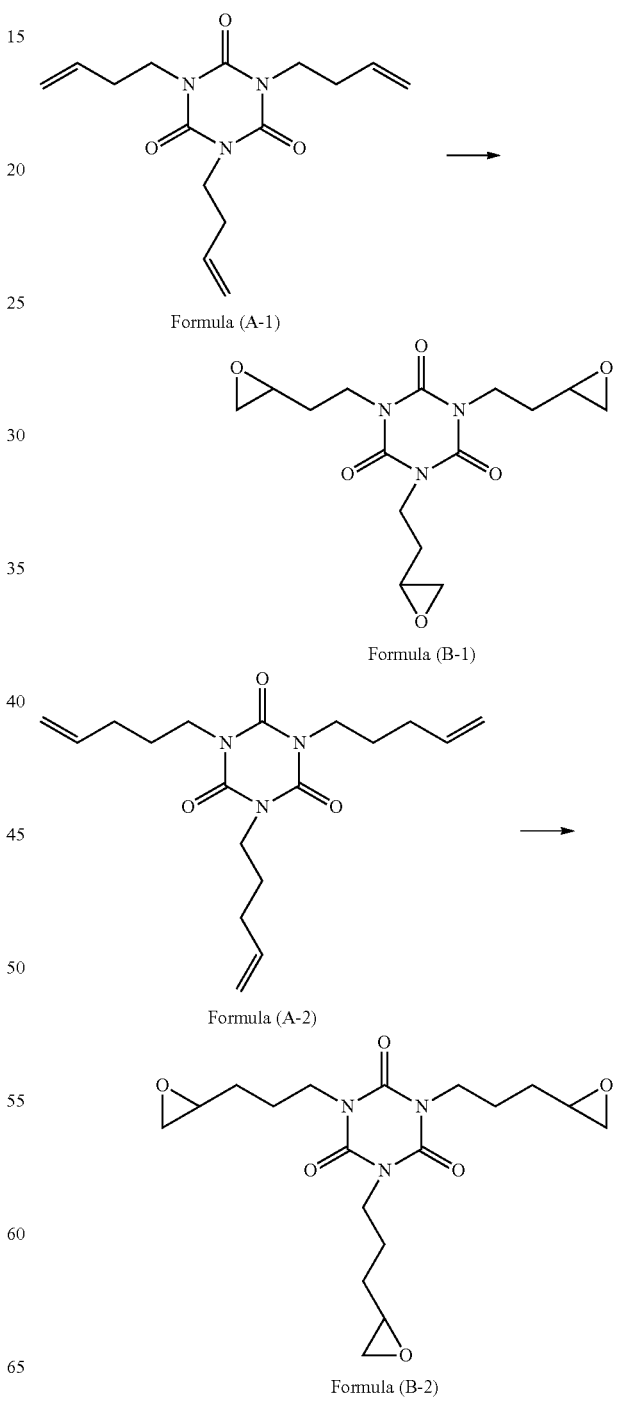

Formula (A-1)

Formula (B-1)

Formula (A-2)

Formula (B-2)

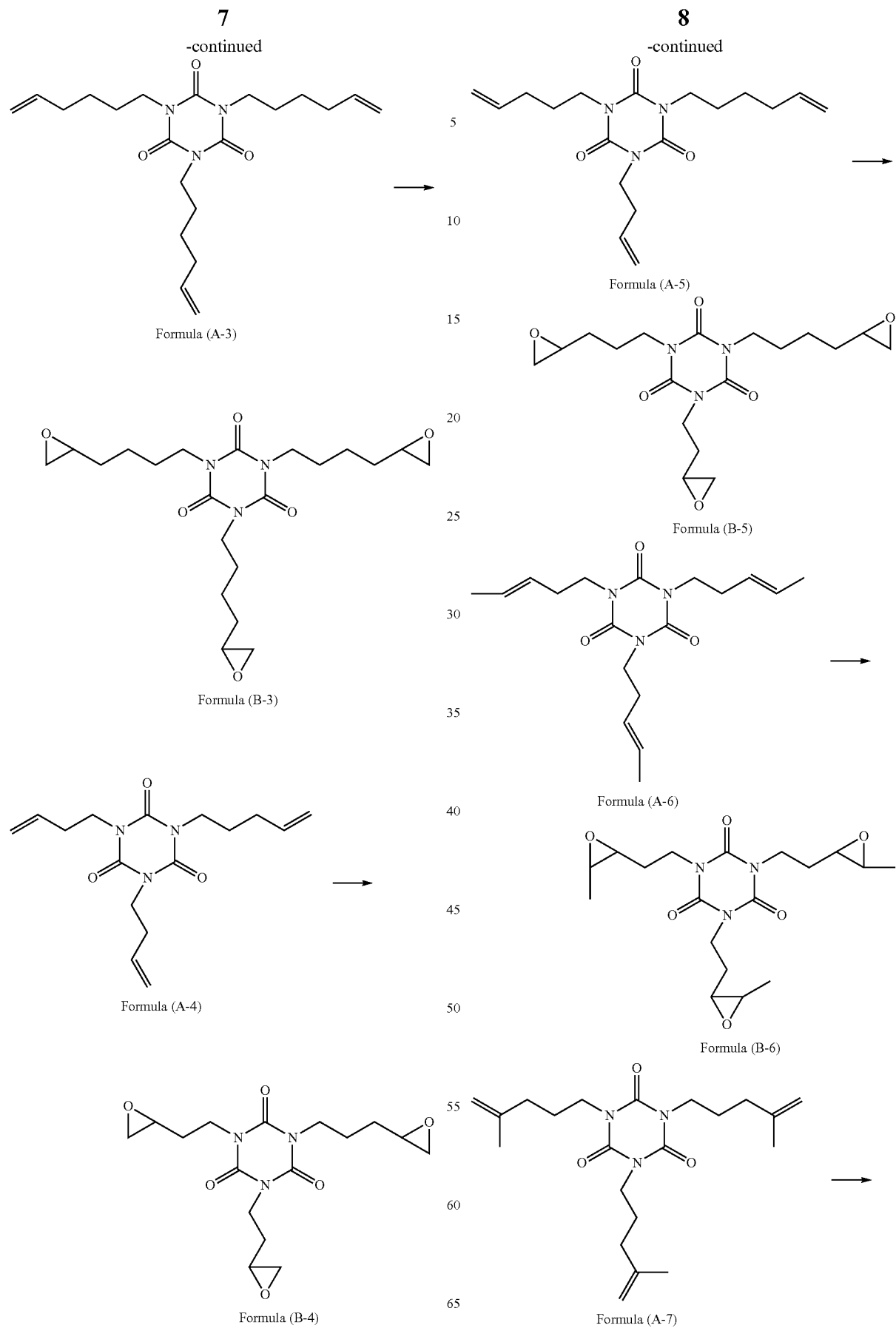

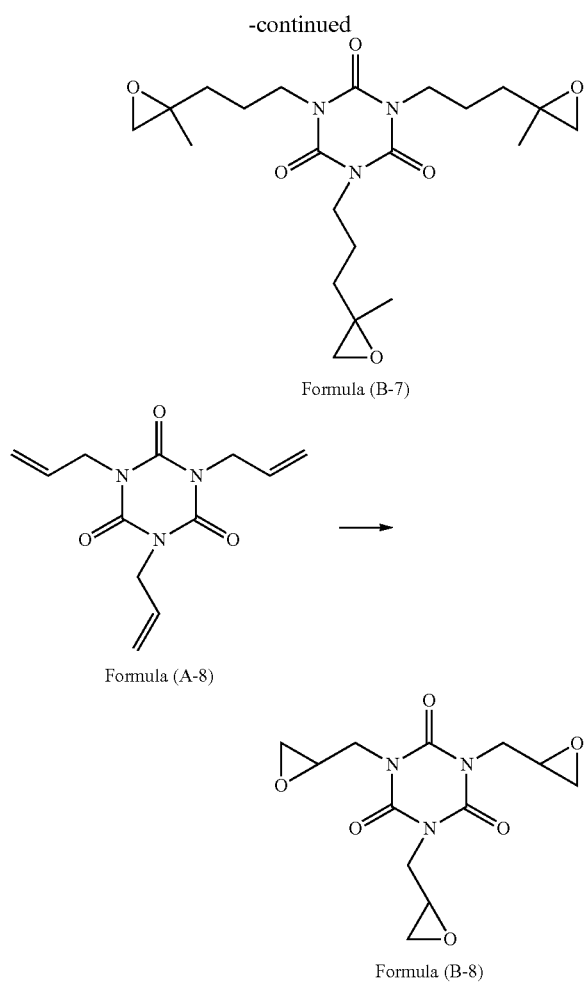

Formula (B-7)

Formula (A-8)

Formula (B-8)

In the epoxy compound obtained by the present invention, for example, when a side chain between a triazinetrione ring and a substituted epoxy group on the triazinetrione ring is elongated, decrease in intermolecular hydrogen bonds cause a hindrance of stacking of triazine, and as a result, liquefaction is achieved. When completeness of a curing reaction of the epoxy group in the epoxy compound is improved, the glass transition temperature of a cured product of the epoxy compound is stabilized. As a result, the cross-linking density is made stable even in a heating environment. Therefore, toughness can be maintained. Further, since the curing reaction of the epoxy group is completed in an early stage of curing, the flexural strength and elasticity of the cured product are made stable. Moreover, water absorption caused by a hydroxy group produced by hydrolysis of an unreacted epoxy group and carboxylic acid produced by hydrolysis of an unreacted acid anhydride (a curing agent) can be suppressed. Therefore, a cured product having a small change in water absorption ratio is obtained.

It is considered that the effects are achieved by involving all the epoxy groups in a reaction, resulting in a cured product having high toughness. This is because an epoxy ring via a long chain alkylene group has a large degree of freedom and high reactivity.

A liquid epoxy compound having a long chain alkylene group can be optically or thermally cured using a photoacid generator or a thermal acid generator.

A photo-curing material using the liquid epoxy compound obtained by the present invention has characteristics such as fast curing, transparency, and small curing shrinkage, and can be used for coating and adhesion of an electronic article, an optical article, and a precision mechanical article. For example, the photo-curing material can be used for adhesion of an optical element such as a lens of a cell phone and a camera, a light-emitting diode (LED), and a semiconductor laser (LD), a liquid crystal panel, a biochip, and a part such as a lens and a prism of a camera, a magnetic part of a hard disk of a personal computer, and the like, a pickup (a part capturing optical information reflected from a disc) of a CD or DVD player, a cone and a coil of a speaker, a magnet of a motor, a circuit substrate, an electronic part, and a part inside an engine of an automobile, and the like.

The epoxy compound obtained by the present invention can be applied to a hard coating material for surface protection of an automobile body, a lamp, an electrical appliance, a construction material, a plastic, and the like, for example, bodies of an automobile and a motorbike, a lens and a mirror of a head light, a plastic lens of glasses, a cell phone, a game machine, an optical film, and an ID card.

Further, the epoxy compound obtained by the present invention can be applied to an ink material for printing on a metal such as aluminum, a plastic, and the like, for example, an ink for printing on a card such as a credit card and a membership card, and on a switch and a keyboard of an electrical appliance and office automation equipment, and an ink for an inkjet printer for CD, DVD, and the like.

Moreover, the epoxy compound obtained by the present invention can be applied to a technique for forming a complicated solid object by curing a resin in combination with three-dimensional CAD, stereolithography such as modeling of an industrial product, coating of optical fibers, adhesion, optical waveguide, thick film resist (for MEMS), and the like.

The olefin compound used in the present invention can be obtained by a reaction of cyanuric acid or cyanurate with an unsaturated alcohol having a carbon atom number of 3 to 9 or the unsaturated alcohol having a protected hydroxyl group in a solvent. In this reaction, an alkaline substance may be used. The unsaturated alcohol or the unsaturated alcohol having a protected hydroxyl group may have a carbon atom number of 4 to 6.

Examples of the alkaline substance used in the reaction include sodium hydroxide, sodium carbonate, potassium carbonate, potassium bicarbonate, and triethylamine. The alkaline substance may be used at a ratio of 1 to 10 mol to 1 mol of cyanuric acid or cyanurate.

Examples of the solvent used in the reaction include N-methylpyrrolidone, N,N-dimethyl formamide, N,N-dimethyl acetamide, 1,3-dimethyl-2-imidazolidinone, and dimethylsulfoxide.

Examples of the cyanurate include trisodium cyanurate and tripotassium cyanurate that are derived from cyanuric acid.

In the reaction, cyanuric acid or cyanurate can be reacted with an unsaturated alcohol having a carbon atom number of 3 to 9 or the unsaturated alcohol having a protected hydroxyl group, for example, at a ratio of the alcohol having a carbon atom number of 3 to 9 or the unsaturated alcohol having a protected hydroxyl group of 0.3 to 9 mol or 0.3 to 27 mol to 1 mol of cyanuric acid or cyanurate. Further, a large excess of the unsaturated alcohol or the unsaturated alcohol having a protected hydroxyl group may be used.

In order to selectively obtain a trimer by involving a proper amount of unsaturated alcohol that is relatively expensive or the unsaturated alcohol having a protected hydroxyl group in the reaction, the unsaturated alcohol or the unsaturated alcohol having a protected hydroxyl group can be subjected to the reaction within a range deviating from the equivalent weight ratio.

Specifically, in the reaction, cyanuric acid or cyanurate can be reacted with the unsaturated alcohol having a carbon atom number of 3 to 9 or the unsaturated alcohol having a protected hydroxyl group, for example, at a ratio of the unsaturated alcohol having a carbon atom number of 3 to 9 or the unsaturated alcohol having a protected hydroxyl group of 0.3 to 5 mol to 1 mol of cyanuric acid or cyanurate.

For example, 1 mol of cyanuric acid can be reacted with 1 to 5 mol or 2 to 5 mol of the unsaturated alcohol having a carbon atom number of 3 to 9 or the unsaturated alcohol having a protected hydroxyl group. 1 mol of cyanurate can be reacted with 0.3 to 1 mol or 0.3 to 2 mol of the unsaturated alcohol having a carbon atom number of 3 to 9 or the unsaturated alcohol having a protected hydroxyl group.

Therefore, when cyanurate is used, a trimer can be selectively produced using a relatively expensive unsaturated alcohol in an amount that is equal to or less than the equivalent weight ratio.

This is considered as follows. Cyanuric acid and cyanurate have low solubility in a solvent. In particular, cyanurate has lower solubility in a solvent than cyanuric acid. For example, in a reaction of 1 mol of cyanurate (having three N—Na groups in a molecule) with 1 mol of unsaturated alcohol or the unsaturated alcohol having a protected hydroxyl group, one N—Na group in one molecule of cyanuric acid is first reacted with the unsaturated alcohol or the unsaturated alcohol having a protected hydroxyl group during a reaction process, and an intermediate in which the group in cyanuric acid is substituted with one alkenyl group is produced. Therefore, it is considered that the solubility of the molecule (intermediate) in a solvent is improved. The reactivity of the intermediate of which the solubility in a solvent is improved is enhanced as compared with another cyanurate (unsubstituted), and another group of the intermediate may be substituted with an alkenyl group and yet another group may be then substituted with another alkenyl group to synthesize triolefin isocyanurate. This pattern is shown even in a case of cyanuric acid, but it is considered that a reaction of cyanurate having lower solubility markedly proceeds.

As an additive in the reaction, halogenated metal such as potassium bromide and potassium iodide can be used. The halogenated metal can be used in an amount of 0.01 to 1 mol relative to 1 mol of isocyanuric acid. In particular, in a reaction of isocyanuric acid with the unsaturated alcohol or the unsaturated alcohol having a protected hydroxyl group, it is preferable that the additive be added.

The reaction can be carried out at the temperature of 20 to 100° C. for 1 to 20 hours.

Examples of the unsaturated alcohol or the unsaturated alcohol having a protected hydroxyl group for synthesis of the triolefin compound include an unsaturated alcohol having a carbon atom number of 3 to 9 or the unsaturated alcohol having a protected hydroxyl group thereof. The carbon atom number of 3 to 9 represents a carbon atom number of unsaturated hydrocarbon group except for a protecting group.

Examples of the protecting group include p-toluenesulfonyl group, o-nitrobenzenesulfonyl group, and methanesulfonyl group. p-toluenesulfonyl group and methanesulfonyl group are preferred. In particular, methanesulfonyl group is preferably used since the yield of olefin compound to be obtained is high.

The unsaturated alcohol or the unsaturated alcohol having a protected hydroxyl group is linear or branched unsaturated alcohol shown below. In the following formulae, $X^1$ is a hydrogen atom, a p-toluenesulfonyl group, an o-nitrobenzenesulfonyl group, or a methanesulfonyl group.

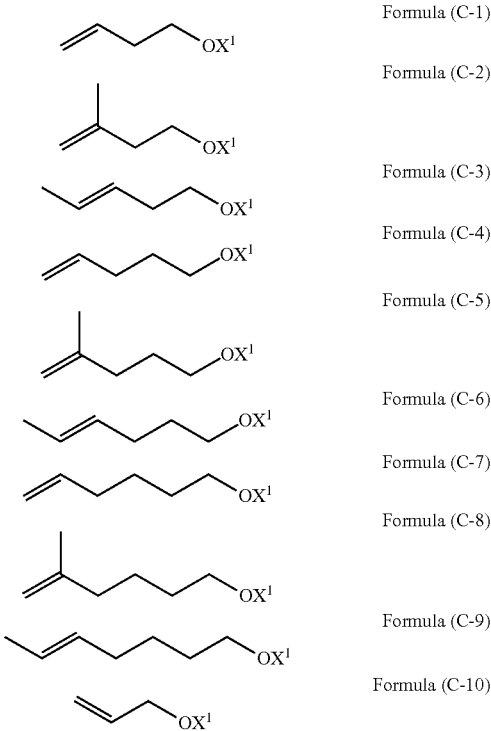

The unsaturated alcohol having the protected hydroxyl group is obtained by a reaction of unsaturated alcohol having a carbon atom number of 3 to 9 with p-toluenesulfonyl halide, o-nitrobenzenesulfonyl halide, or methanesulfonyl halide in the presence of an alkaline substance in a solvent. As the halide, a halide such as fluoride, chloride, bromide, and iodide is used.

Examples of the alkaline substance used in the reaction include sodium hydroxide, sodium carbonate, potassium carbonate, potassium bicarbonate, and triethylamine.

Examples of the solvent used in the reaction include N-methylpyrrolidone, N,N-dimethyl formamide, N,N-dimethyl acetamide, 1,3-dimethyl-2-imidazolidinone, dimethyl sulfoxide, and toluene.

A reaction of cyanuric acid or cyanurate with the unsaturated alcohol having a carbon atom number of 3 to 9 or the unsaturated alcohol having a protected hydroxyl group is shown below. In the following formulae, $X^1$ is a hydrogen atom, a p-toluenesulfonyl group, an o-nitrobenzenesulfonyl group, or a methanesulfonyl group, and $X^2$ is a hydrogen atom, sodium, or potassium.

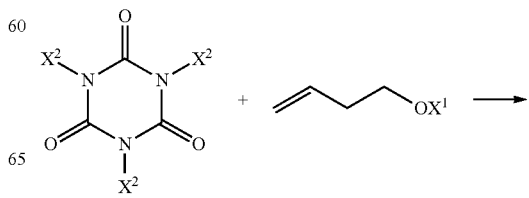

-continued
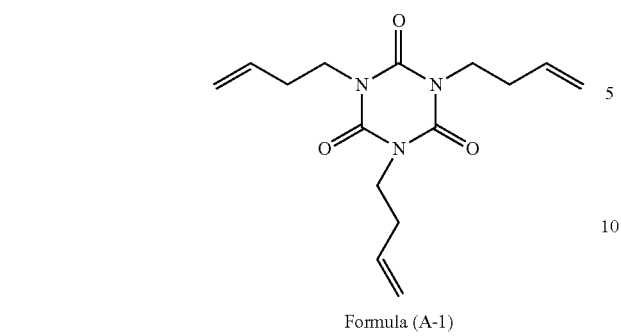
Formula (A-1)
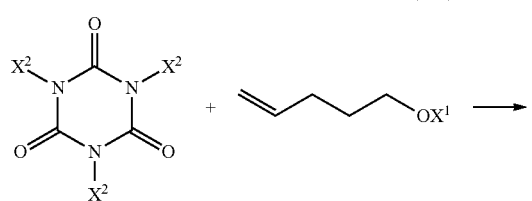
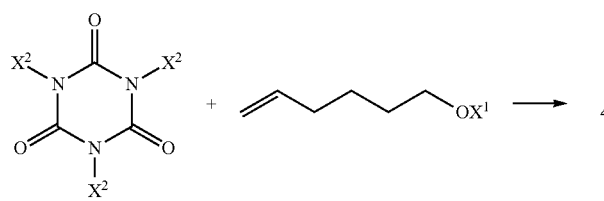
Formula (A-2)
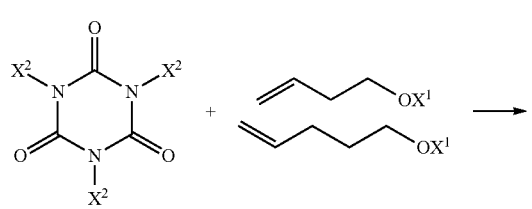
Formula (A-3)
-continued
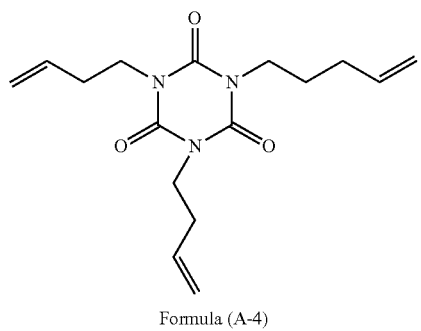
Formula (A-4)
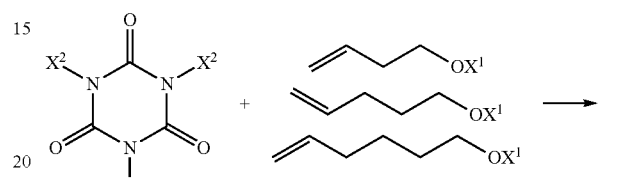
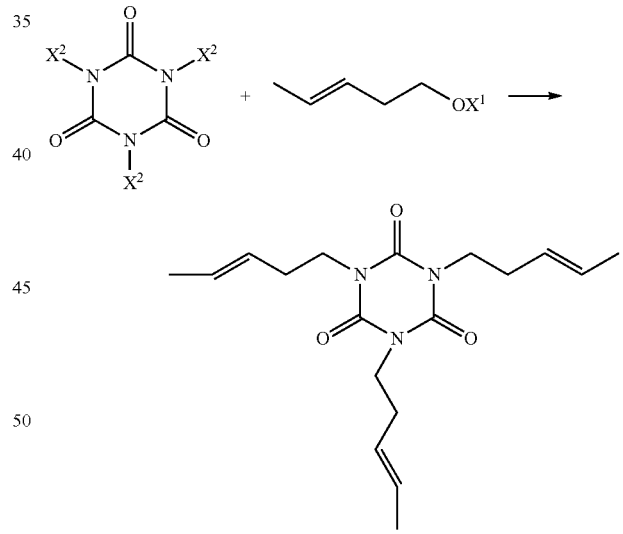
Formula (A-5)
Formula (A-6)
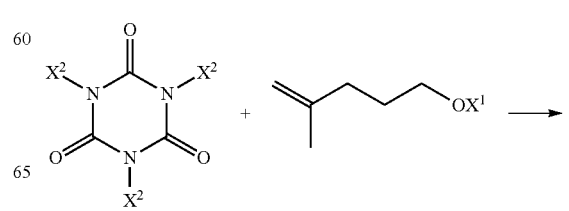

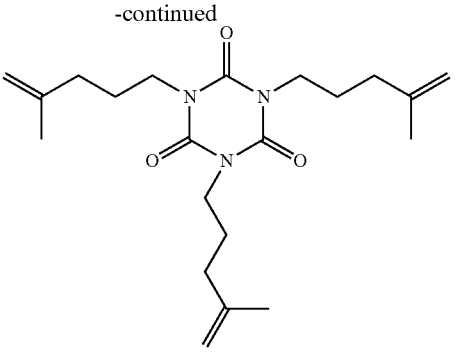

Formula (A-7)

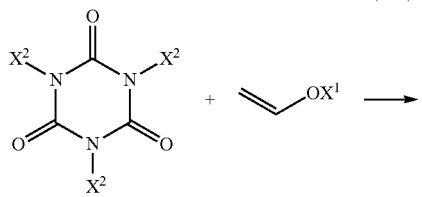

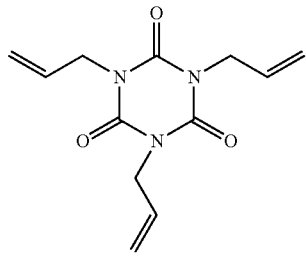

Formula (A-8)

EXAMPLES

Hereinafter, the present invention will be described more specifically with reference to Examples, but the present invention is not limited to the following Examples.

In Examples, devices used for analysis of samples are as follows.
[HPLC (high performance liquid chromatography)]
Device: 1200 Series manufactured by Agilent Technologies
[GC (gas chromatography)]
Device: 7890A manufactured by Agilent Technologies

Example 1

1,3,5-tris-(4-pentenyl)-isocyanurate (18.0 g, 54.0 mmol), acetonitrile (22.1 g, 540 mmol), and methanol (54 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution containing 1-hydroxyethane-1, 1-diphosphonic acid having a concentration of 170 ppm was added over 30 hours in a plurality of batches so that the pH of a reaction medium was maintained at 8.5 to 10.5. After the 30-hour reaction, the reaction medium was analyzed by GC. The conversion ratio of a double bond in the olefin compound into an epoxy group was 99%. The amount of oxygen gas generated in the reaction was 37 mL.

The resultant solution was analyzed by HPLC, and the yield of 1,3,5-tris-(4,5-epoxypentyl)-isocyanurate was confirmed to be 83%.

Example 2

1,3,5-tris-(4-pentenyl)-isocyanurate (18.0 g, 54.0 mmol), acetonitrile (22.1 g, 540 mmol), and methanol (54 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution containing nitrilotris(methylenephosphonic acid) having a concentration of 340 ppm was added over 30 hours in a plurality of batches so that the pH of a reaction medium was maintained at 8.5 to 10.5. After the 30-hour reaction, the reaction medium was analyzed by GC. The conversion ratio of a double bond in the olefin compound into an epoxy group was 99%. The amount of oxygen gas generated in the reaction was 30 mL.

The resultant solution was analyzed by HPLC, and the yield of 1,3,5-tris-(4,5-epoxypentyl)-isocyanurate was confirmed to be 84%.

Example 3

1,3,5-tris-(4-pentenyl)-isocyanurate (18.0 g, 54.0 mmol), acetonitrile (22.1 g, 540 mmol), and methanol (54 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution containing N,N,N',N'-ethylenediaminetetrakis(methylenephosphonic acid) having a concentration of 340 ppm was added over 30 hours in a plurality of batches so that the pH of a reaction medium was maintained at 8.5 to 10.5. After the 30-hour reaction, the reaction medium was analyzed by GC. The conversion ratio of a double bond in the olefin compound into an epoxy group was 99%. The amount of oxygen gas generated in the reaction was 31 mL.

The resultant solution was analyzed by HPLC, and the yield of 1,3,5-tris-(4,5-epoxypentyl)-isocyanurate was confirmed to be 84%.

Example 4

1,3,5-tris-(4-pentenyl)-isocyanurate (18.0 g, 54.0 mmol), acetonitrile (22.1 g, 540 mmol), and methanol (54 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution containing methylenedihosphonic acid having a concentration of 340 ppm was added over 30 hours in a plurality of batches so that the pH of a reaction medium was maintained at 8.5 to 10.5. After the 30-hour reaction, the reaction medium was analyzed by GC. The conversion ratio of a double bond in the olefin compound into an epoxy group was 99%. The amount of oxygen gas generated in the reaction was 110 mL.

The resultant solution was analyzed by HPLC, and the yield of 1,3,5-tris-(4,5-epoxypentyl)-isocyanurate was confirmed to be 84%.

Example 5

1,3,5-tris-(4-pentenyl)-isocyanurate (18.0 g, 54.0 mmol), acetonitrile (22.1 g, 540 mmol), and methanol (54 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution containing 1-hydroxyethane-1,1-diphosphonic acid tetrasodium salt having a concentration of 340 ppm was added over 30 hours in a plurality of batches so that the pH of a reaction medium was maintained at 8.5 to 10.5. After the 30-hour reaction, the reaction medium was analyzed by GC. The conversion ratio of a double bond in the olefin compound into an epoxy group was 99%. The amount of oxygen gas generated in the reaction was 17 mL.

The resultant solution was analyzed by HPLC, and the yield of 1,3,5-tris-(4,5-epoxypentyl)-isocyanurate was confirmed to be 84%.

Example 6

1,3,5-tris-(4-pentenyl)-isocyanurate (18.0 g, 54.0 mmol), acetonitrile (22.1 g, 540 mmol), and methanol (54 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution containing aminomethylphosphonic acid having a concentration of 340 ppm was added over 30 hours in a plurality of batches so that the pH of a reaction medium was maintained at 8.5 to 10.5. After the 30-hour reaction, the reaction medium was analyzed by GC. The conversion ratio of a double bond in the olefin compound into an epoxy group was 99%. The amount of oxygen gas generated in the reaction was 78 mL.

The resultant solution was analyzed by HPLC, and the yield of 1,3,5-tris-(4,5-epoxypentyl)-isocyanurate was confirmed to be 85%.

Example 7

1,3,5-tris-(3-butenyl)-isocyanurate (15.7 g, 54.0 mmol), acetonitrile (22.1 g, 540 mmol), and methanol (47 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution containing 1-hydroxyethane-1,1-diphosphonic acid having a concentration of 170 ppm was added over 30 hours in a plurality of batches so that the pH of a reaction medium was maintained at 8.5 to 10.5. After the 30-hour reaction, the reaction medium was analyzed by GC. The conversion ratio of a double bond in the olefin compound into an epoxy group was 99%. The amount of oxygen gas generated in the reaction was 86 mL.

The resultant solution was purified and isolated, and the yield of 1,3,5-tris-(3,4-epoxybutyl)-isocyanurate was confirmed to be 60%.

Example 8

1,3,5-tris-(5-hexenyl)-isocyanurate (20.3 g, 54.0 mmol), acetonitrile (22.1 g, 540 mmol), and methanol (61 g) were mixed, and the temperature was set to 20° C. An aqueous 35% by mass hydrogen peroxide solution (37.1 mL, 432 mmol) was added dropwise in a plurality of batches over 20 hours. At the same time as onset of the dropwise addition of the aqueous 35% by mass hydrogen peroxide solution, an aqueous 8% by mass sodium hydroxide solution containing 1-hydroxyethane-1,1-diphosphonic acid having a concentration of 170 ppm was added over 30 hours so that the pH of a reaction medium was maintained at 8.5 to 10.5. After the 30-hour reaction, the reaction medium was analyzed by GC. The conversion ratio of a double bond in the olefin compound into an epoxy group was 99%. The amount of oxygen gas generated in the reaction was 24 mL.

The resultant solution was purified and isolated, and the yield of 1,3,5-tris-(5,6-epoxyhexyl)-isocyanurate was confirmed to be 93%.

Comparative Example 1

1,3,5-tris-(4-pentenyl)-isocyanurate (18.0 g, 54.0 mmol), acetonitrile (22.1 g, 540 mmol), and methanol (54 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution was added over 30 hours in a plurality of batches so that the pH of a reaction medium was maintained at 8.5 to 10.5. After the 30-hour reaction, the reaction medium was analyzed by GC. The conversion ratio of a double bond in the olefin compound into an epoxy group was 99%. The amount of oxygen gas generated in the reaction was 148 mL.

The resultant solution was analyzed by HPLC, and the yield of 1,3,5-tris-(4,5-epoxypentyl)-isocyanurate was confirmed to be 84%.

Comparative Example 2

1,3,5-tris-(4-pentenyl)-isocyanurate (18.0 g, 54.0 mmol), acetonitrile (22.1 g, 540 mmol), and methanol (54 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution containing 1-hydroxyethane-1,1-diphosphonic acid having a concentration of 170 ppm was added over 30 hours in a plurality of batches so that the pH of a reaction medium was maintained at 6.5 to 7.5. After the 30-hour reaction, the reaction medium was analyzed by GC. The conversion ratio of a double bond in the olefin compound into an epoxy group was 3%. The amount of oxygen gas generated in the reaction was 5 mL.

Comparative Example 3

1,3,5-tris-(4-pentenyl)-isocyanurate (18.0 g, 54.0 mmol), acetonitrile (22.1 g, 540 mmol), and methanol (54 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution containing 1-hydroxyethane-1,1-diphosphonic acid having a concentration of 170 ppm was added over 30 hours in a plurality of batches so that the pH of a reaction medium was maintained at 2.0 to 3.0. After the 30-hour reaction, the reaction medium was analyzed by GC. The conversion ratio of a double bond in the olefin compound into an epoxy group was 0%. The amount of oxygen gas generated in the reaction was 0 mL.

Comparative Example 4

1,3,5-tris-(4-pentenyl)-isocyanurate (18.0 g, 54.0 mmol), acetonitrile (22.1 g, 540 mmol), and methanol (54 g) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution containing 1-hydroxyethane-1,1-diphosphonic acid having a concentration of 170 ppm was added over 30 hours in a plurality of batches so that the pH of a reaction medium was maintained at 12.0 to 13.0. After the 30-hour reaction, the reaction medium was analyzed by GC. The conversion ratio of a double bond in the olefin compound into an epoxy group was 0%. The added aqueous 35% by mass hydrogen peroxide solution was all decomposed to generate a large amount of oxygen gas.

Comparative Example 5

1,3,5-tris-(4-pentenyl)-isocyanurate (18.0 g, 54.0 mmol), acetonitrile (22.1 g, 540 mmol), methanol (54 g), and an aqueous 60% by mass 1-hydroxyethane-1,1-diphosphonic acid solution (16.3 mg) were mixed, and the temperature was set to 20° C. An aqueous 35% by mass hydrogen peroxide solution (37.1 mL, 432 mmol) was added dropwise over 20 hours. At the same time as onset of the dropwise addition of the aqueous 35% by mass hydrogen peroxide solution, an aqueous 8% by mass sodium hydroxide solution was added over 30 hours in a plurality of batches so that the pH of a reaction medium was maintained at 8.5 to 10.5. After the 30-hour reaction, the reaction medium was analyzed by GC. The conversion ratio of a double bond in the olefin compound into an epoxy group was 99%. The amount of oxygen gas generated in the reaction was 355 mL.

The resultant solution was analyzed by HPLC, and the yield of 1,3,5-tris-(4,5-epoxypentyl)-isocyanurate was confirmed to be 84%.

INDUSTRIAL APPLICABILITY

In the method for producing an epoxy compound by a reaction of an olefin compound with hydrogen peroxide, the epoxy compound can be stably and safely produced using a hydrogen peroxide stabilizer for decreasing the generation of an oxygen gas by decomposition of hydrogen peroxide. Therefore, large-scale production of epoxy compound is possible in the present invention.

The invention claimed is:

1. A method for producing an epoxy compound, the method comprising:
reacting an olefin compound with hydrogen peroxide in the presence of an alkylphosphonic acid or a salt thereof in such a reaction medium that the pH is maintained within a range of more than 7.5 and less than 12.0, wherein the olefin compound is 1,3,5-tris-(alkenyl)-isocyanurate.

2. The method according to claim 1, wherein the alkenyl group in the olefin compound is 3-butenyl group, 4-pentenyl group, 5-hexenyl group, 6-heptenyl group, or 7-octenyl group.

3. The method according to claim 1, wherein the epoxy compound is 1,3,5-tris-(epoxyalkyl)-isocyanurate.

4. The method according to claim 3, wherein the epoxyalkyl group in the epoxy compound is 3,4-epoxybutyl group, 4,5-epoxypentyl group, 5,6-epoxyhexyl group, 6,7-epoxyheptyl group, or 7,8-epoxyoctyl group.

5. The method according to claim 1, wherein the reaction medium is such a reaction medium that the pH is maintained within a range of 8.0 to 10.5.

6. The method according to claim 1, wherein the reaction medium contains a nitrile compound.

7. The method according to claim 6, wherein the nitrile compound is acetonitrile.

8. The method according to claim 1, wherein the pH is maintained by addition of an aqueous alkaline solution containing the alkylphosphonic acid or salt thereof.

9. The method according to claim 1, wherein an amount of the alkylphosphonic acid or salt thereof in the reaction medium is 0.0001 to 1.0% by mass relative to the 1,3,5-tris-(alkenyl)-isocyanurate.

* * * * *